United States Patent
Kelly

Patent Number: 5,611,099
Date of Patent: Mar. 18, 1997

[54] HANDS AND ARMS CLEANING APPARATUS

[76] Inventor: Philip C. Kelly, 290 New Hermitage Rd., Rome, Ga. 30161

[21] Appl. No.: 595,651

[22] Filed: Feb. 2, 1996

[51] Int. Cl.$^6$ ................................. A46B 13/06
[52] U.S. Cl. ........................................... 15/21.1
[58] Field of Search ................... 15/3, 21.1, 104.92; 422/292

[56] References Cited

U.S. PATENT DOCUMENTS

| | | | |
|---|---|---|---|
| 2,814,081 | 11/1957 | Stevenson | 422/292 |
| 3,066,336 | 12/1962 | Stobbe | 15/21.1 |
| 3,332,099 | 7/1967 | Reiter | 15/21.1 |
| 3,439,370 | 4/1969 | McLaughlin | 15/21.1 |
| 4,180,884 | 1/1980 | Hess et al. | 15/21.1 |
| 4,891,857 | 1/1990 | Pinsonneault | 15/21.1 |

Primary Examiner—David Scherbel
Assistant Examiner—Randall E. Chin

[57] ABSTRACT

A hands and arms cleaning apparatus comprised of a housing receiving a water supply line therein and having a water drain secured thereto. A pair of hand receiving holes are disposed within a front surface of the housing. A plurality of water sprayers are secured to an interior of an upper surface of the housing. The plurality of water sprayers are each coupled with the water supply line. A plurality of brushing members are rotatably positioned within a hollow interior of the housing.

4 Claims, 3 Drawing Sheets

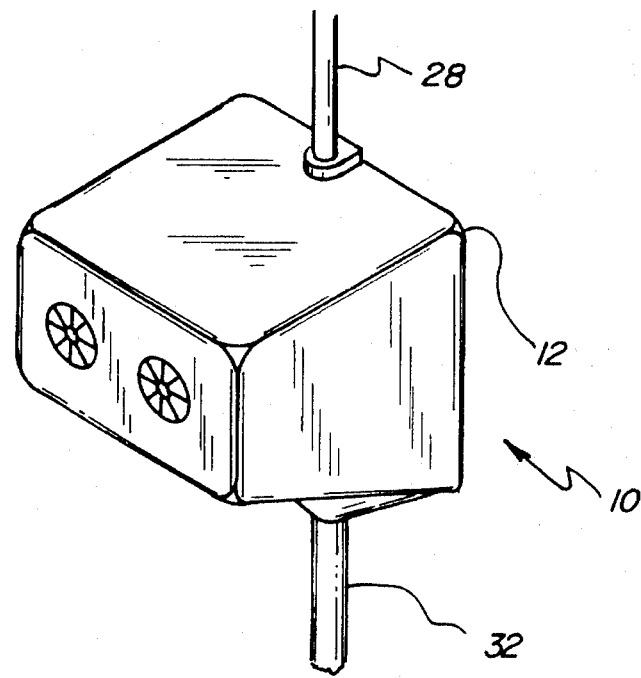
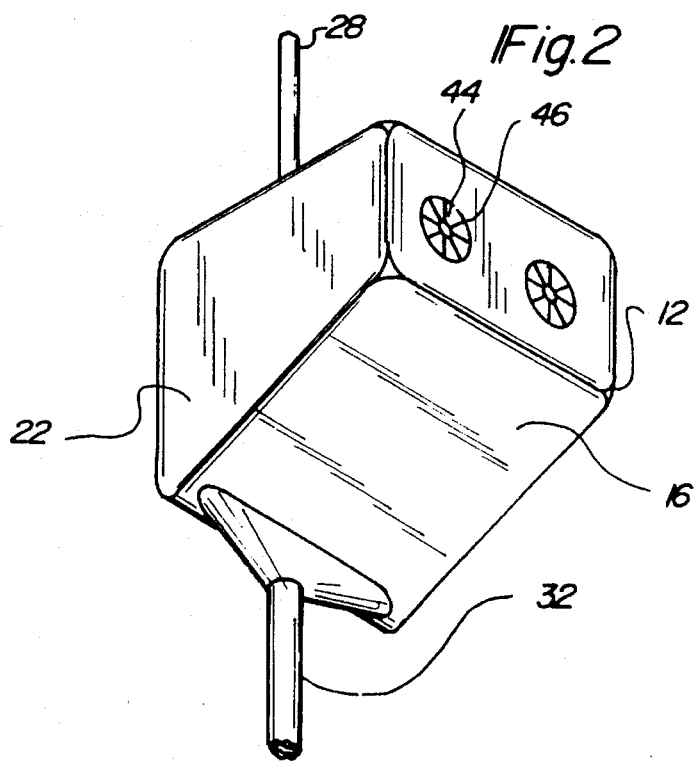

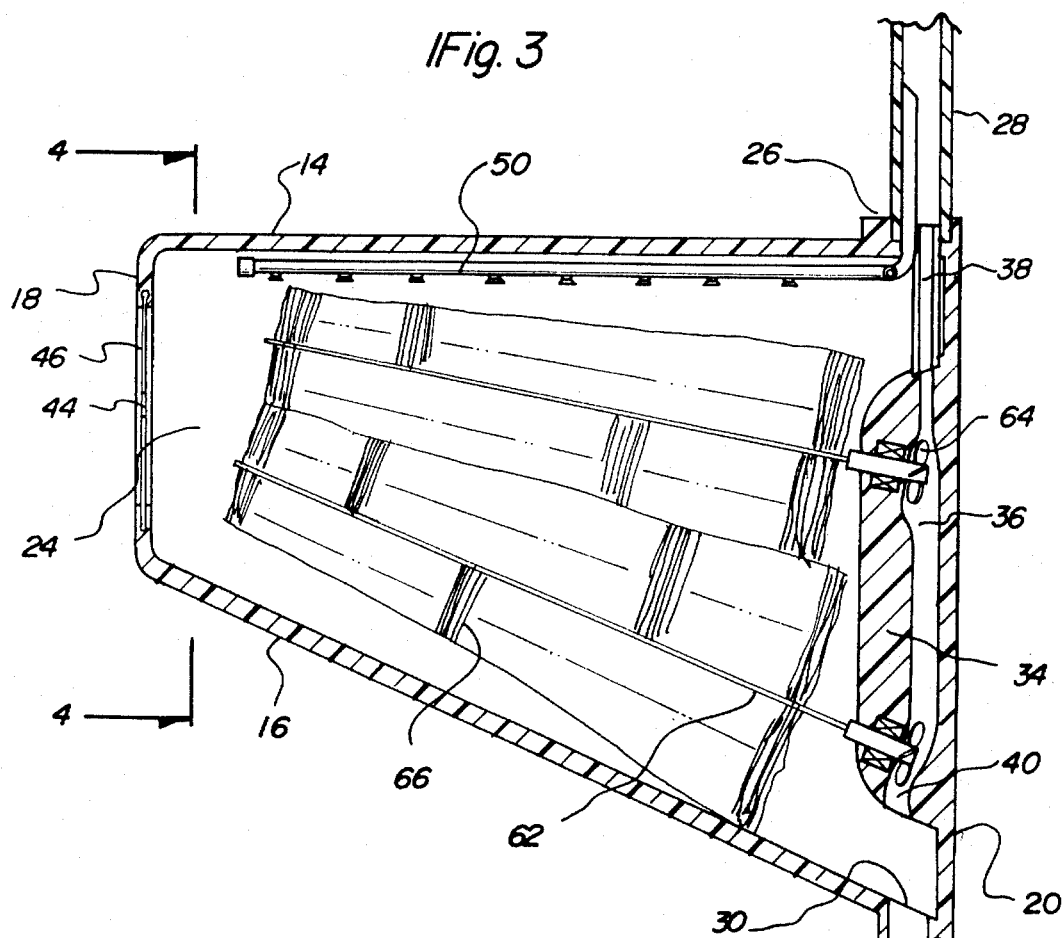
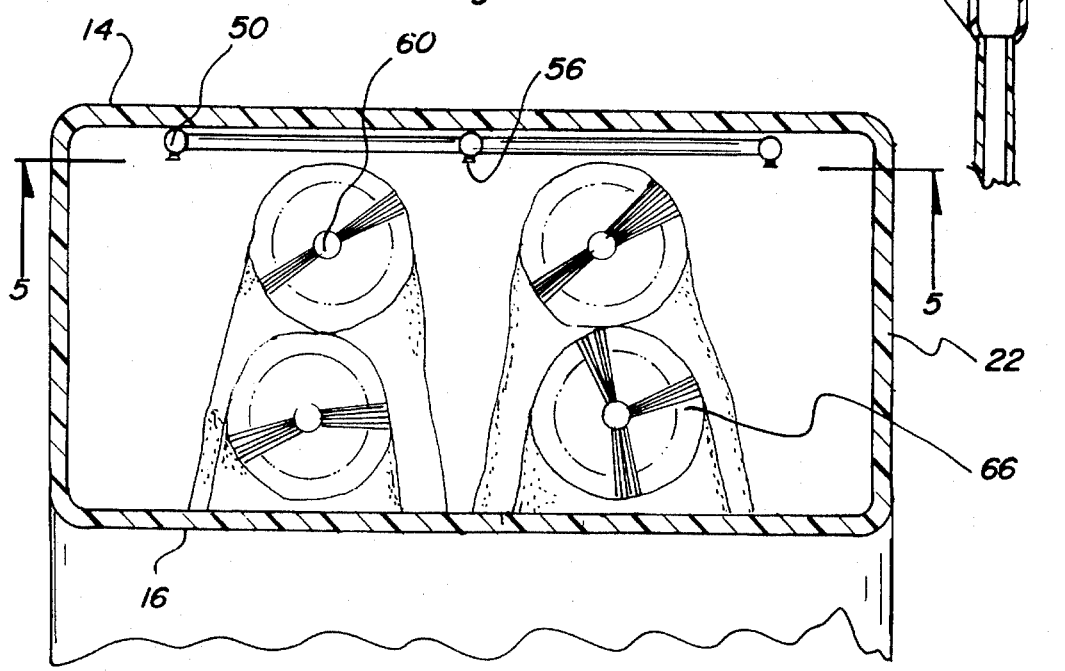

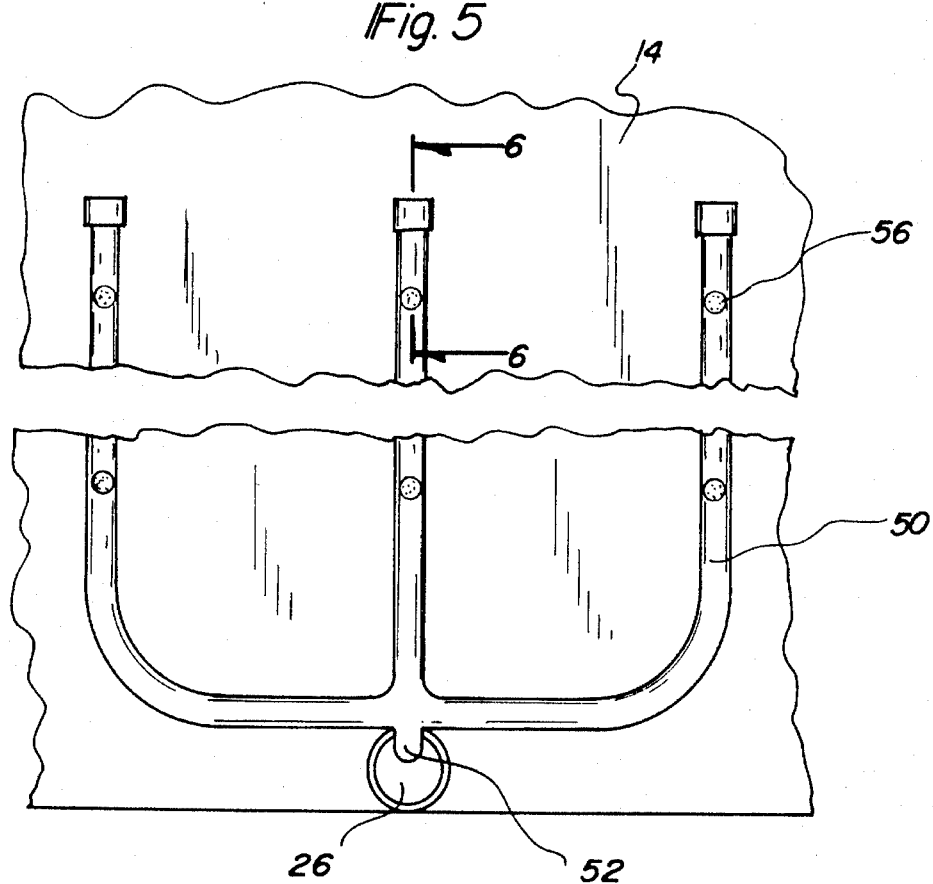
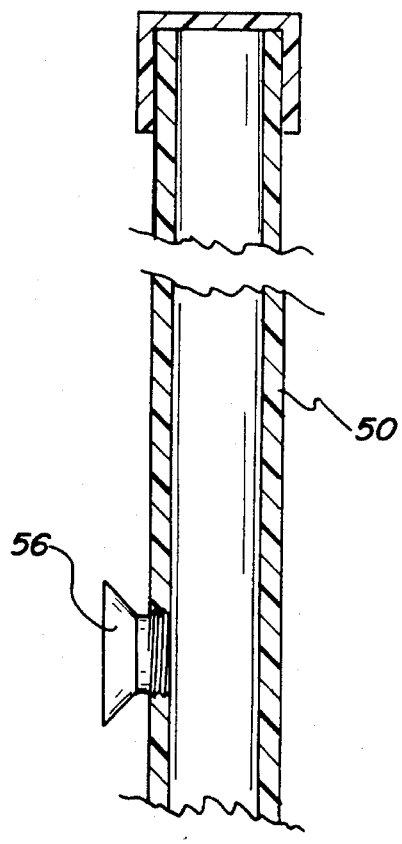

HANDS AND ARMS CLEANING APPARATUS

BACKGROUND OF THE INVENTION

1. Field of the Invention

The present invention relates to a hands and arms cleaning apparatus and more particularly pertains to automatically cleaning hands and arms of a user with a hands and arms cleaning apparatus.

2. Description of the Prior Art

The use of hand washing devices is known in the prior art. More specifically, hand washing devices heretofore devised and utilized for the purpose of automatically washing hands are known to consist basically of familiar, expected and obvious structural configurations, notwithstanding the myriad of designs encompassed by the crowded prior art which have been developed for the fulfillment of countless objectives and requirements.

By way of example, U.S. Pat. No. 3,439,370 to McLaughlin discloses a hand washing machine.

U.S. Pat. No. 4,769,863 to Tegg et al. discloses a hand wash unit.

U.S. Pat. No. Des. 315,196 to Tegg et al. discloses the ornamental design for a portable hand wash unit.

U.S. Pat. No. 4,295,233 to Hinkel et al. discloses an automatic hand washer and dryer.

U.S. Pat. No. 4,606,085 to Davies discloses a hand washing device.

U.S. Pat. No. Des. 272,263 to Lienhard discloses the ornamental design for a hand washer.

While these devices fulfill their respective, particular objective and requirements, the aforementioned patents do not describe a hands and arms cleaning apparatus for automatically cleaning hands and arms of a user.

In this respect, the hands and arms cleaning apparatus according to the present invention substantially departs from the conventional concepts and designs of the prior art, and in doing so provides an apparatus primarily developed for the purpose of automatically cleaning hands and arms of a user.

Therefore, it can be appreciated that there exists a continuing need for new and improved hands and arms cleaning apparatus which can be used for automatically cleaning hands and arms of a user. In this regard, the present invention substantially fulfills this need.

SUMMARY OF THE INVENTION

In the view of the foregoing disadvantages inherent in the known types of hand washing devices now present in the prior art, the present invention provides an improved hands and arms cleaning apparatus. As such, the general purpose of the present invention, which will be described subsequently in greater detail, is to provide a new and improved hands and arms cleaning apparatus and method which has all the advantages of the prior art and none of the disadvantages.

To attain this, the present invention essentially comprises a housing having an upper surface, a lower surface, a front surface, a rear surface, two side surfaces, and a hollow interior. The upper surface has an aperture therethrough adjacent the rear surface. The aperture receives a water supply line therein. The lower surface has an aperture therethrough adjacent the rear surface. The aperture of the lower surface has a water drain secured thereto. The housing has an interior housing secured to an interior of the rear surface. The interior housing has a water channel extending therethrough. The water channel has an upper end coupled with the aperture of the upper surface for connection with the water supply line. The water channel has a lower end coupled with the aperture of the lower surface for connection with the water drain secured thereto. A pair of hand receiving holes are disposed within the front surface of the housing. The holes each have flexible sealing members radially arranged therein. A plurality of water sprayers are secured to an interior of the upper surface of the housing. The plurality of water sprayers are each connected to a central water line. The central water line extends through the aperture in the upper surface of the housing to couple with the water supply line. A plurality of brushing members are positioned within the hollow interior of the housing. Each of the brushing members has a rod extending inwardly of the interior housing and into the water channel. Each rod has a propeller secured to an end portion thereof within the water channel. Each of the rods have bristles extending radially therefrom.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved hands and arms cleaning apparatus which has all the advantages of the prior art hand washing devices and none of the disadvantages.

It is another object of the present invention to provide a new and improved hands and arms cleaning apparatus which may be easily and efficiently manufactured and marketed.

It is a further object of the present invention to provide a new and improved hands and arms cleaning apparatus which is of durable and reliable construction.

An even further object of the present invention is to provide a new and improved hands and arms cleaning apparatus which is susceptible of a low cost of manufacture with regard to both materials and labor, and which accordingly is then susceptible of low prices of sale to the consuming public, thereby making such a hands and arms cleaning apparatus economically available to the buying public.

Still yet another object of the present invention is to provide a new and improved hands and arms cleaning apparatus which provides in the apparatuses and methods of the prior art some of the advantages thereof, while simultaneously overcoming some of the disadvantages normally associated therewith.

Even still another object of the present invention is to provide a new and improved hands and arms cleaning apparatus for automatically cleaning hands and arms of a user.

Lastly, it is an object of the present invention to provide a new and improved hands and arms cleaning apparatus comprised of a housing receiving a water supply line therein and having a water drain secured thereto. A pair of hand receiving holes are disposed within a front surface of the housing. A plurality of water sprayers are secured to an interior of an upper surface of the housing. The plurality of water sprayers are each coupled with the water supply line. A plurality of brushing members are rotatably positioned within a hollow interior of the housing.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective view of the preferred embodiment of the hands and arms cleaning apparatus constructed in accordance with the principles of the present invention.

FIG. 2 is a bottom perspective view of the present invention.

FIG. 3 is a cross-sectional view of the housing of the present invention.

FIG. 4 is a cross-sectional view as taken along line 4—4 of FIG. 3.

FIG. 5 is a cross-sectional view as taken along line 5—5 of FIG. 4.

FIG. 6 is a cross-sectional view as taken along line 6—6 of FIG. 5.

The same reference numerals refer to the same parts through the various Figures.

DESCRIPTION OF THE PREFERRED EMBODIMENT

With reference now to the drawings, and in particular, to FIGS. 1–6 thereof, the preferred embodiment of the new and improved hands and arms cleaning apparatus embodying the principles and concepts of the present invention and generally designated by the reference number 10 will be described.

Specifically, it will be noted in the various Figures that the device relates to a new and improved hands and arms cleaning apparatus for automatically cleaning hands and arms of a user. In its broadest context, the device consists of a housing, a pair of hand receiving holes, a plurality of water sprayers, and a plurality of brushing members. Such components are individually configured and correlated with respect to each other so as to attain the desired objective.

The device 10 includes a housing 12 having an upper surface 14, a lower surface 16, a front surface 18, a rear surface 20, two side surfaces 22, and a hollow interior 24. The upper surface 14 has an aperture 26 therethrough adjacent the rear surface 20. The aperture 26 receives a water supply line 28 therein. The lower surface 16 has an aperture 30 therethrough adjacent the rear surface 20. The aperture 30 of the lower surface 16 has a water drain 32 secured thereto. The housing 12 has an interior housing 34 secured to an interior of the rear surface 20. The interior housing 34 has a water channel 36 extending therethrough. The water channel 36 has an upper end 38 coupled with the aperture 26 of the upper surface 14 for connection with the water supply line 28. The water channel 36 has a lower end 40 aligned with the aperture 30 of the lower surface 16 for fluid communication with the water drain 32 secured thereto.

A pair of hand receiving holes 44 are disposed within the front surface 18 of the housing 12. The holes 44 each have flexible sealing members 46 radially arranged therein.

A plurality of water sprayers 50 are secured to an interior of the upper surface 14 of the housing 12. The plurality of water sprayers 50 are each connected to a central water line 52. The central water line 52 extends through the aperture 26 in the upper surface 14 of the housing 12 to couple with the water supply line 28. The plurality of water sprayers 50 are comprised of water tubes extending along the entire length of the housing 12. Each of the water tubes has a plurality of sprayer heads 56 positioned along their length for dispersement of water through the housing 12.

A plurality of brushing members 60 are positioned within the hollow interior 24 of the housing 12. Each of the brushing members 60 has a rod 62 extending inwardly of the interior housing 24 and into the water channel 36. Each rod 62 has a propeller 64 secured to an end portion thereof within the water channel 36. Each of the rods 62 have bristles 66 extending radially therefrom. The water from the water supply line 28 flows through the water channel 36 causing the propulsion of the propeller's 64 thereby causing the rotating of the brushing members 60. The preferred number of brushing members 60 is four with the brushing members positioned adjacent to the hand receiving holes 44 to rotate about the user's hands and arms when they are placed within the housing 12. Additional water will be sprayed out of the plurality of water sprayers 50 to rinse off any soap that was originally placed on the arms and hands. The excess water is then drained out of the water drain 32. The device 10 can be mounted to a bathroom wall of any establishment or institution.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed as being new and desired to be protected by Letters Patent of the United States is as follows:

1. A hands and arms cleaning apparatus for automatically cleaning hands and arms of a user comprising, in combination:

a housing having an upper surface, a lower surface, a front surface, a rear surface, two side surfaces, and a hollow interior, the upper surface having an aperture therethrough adjacent the rear surface, the aperture receiving a water supply line therein, the lower surface having an aperture therethrough adjacent the rear surface, the aperture of the lower surface having a water drain secured thereto, the housing having an interior housing secured to an interior of the rear surface, the interior housing having a water channel extending therethrough, the water channel having an upper end coupled with the aperture of the upper surface for connection with the water supply line, the water channel having a lower end aligned with the aperture of the lower surface for fluid communication with the water drain secured thereto;

a pair of hand receiving holes disposed within the front surface of the housing, the holes each having flexible sealing members radially arranged therein;

a plurality of water sprayers secured to an interior of the upper surface of the housing, the plurality of water sprayers each connected to a central water line, the central water line extending through the aperture in the upper surface of the housing to couple with the water supply line;

a plurality of brushing members positioned within the hollow interior of the housing, each of the brushing members having a rod extending inwardly of the interior housing into the water channel, each rod having a propeller secured to an end portion thereof within the water channel, each of the rods having bristles extending radially therefrom.

2. A hands and arms cleaning apparatus comprising:

a housing having an upper surface, a lower surface, a front surface, a rear surface, two side surfaces, and a hollow interior, the housing receiving a water supply line therein and having a water drain secured thereto;

a pair of hand receiving holes disposed within the front surface of the housing;

a plurality of water sprayers secured to an interior of the upper surface of the housing, the sprayers disposed above the pair of hand receiving holes, the plurality of water sprayers each coupled with the water supply line;

a plurality of elongated brushing members positioned within the hollow interior of the housing, each of the brushing members having a rotation means wherein the housing has an interior housing secured to an interior of the rear surface, the interior housing having a water channel extending therethrough, the water channel having an upper end coupled with the water supply line, the water channel having a lower end coupled with the water drain.

3. The apparatus as set forth in claim 2 wherein the rotation means of the plurality of brushing members comprises a rod extending inwardly of the interior housing into the water channel from each brushing member, each rod having a propeller secured to an end portion thereof within the water channel, each of the rods having bristles extending radially therefrom.

4. The apparatus as set forth in claim 2 wherein each of the hand receiving holes has flexible sealing members radially arranged therein.

* * * * *